United States Patent [19]

Klemm

[11] Patent Number: Plant 6,995

[45] Date of Patent: Aug. 22, 1989

[54] GERANIUM PLANT NAMED KLEFICE

[75] Inventor: Siegfried Klemm, Stuttgart, Fed. Rep. of Germany

[73] Assignee: Klemm & Sohn, Stuttgart, Fed. Rep. of Germany

[21] Appl. No.: 237,399

[22] Filed: Aug. 29, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new geranium cultivar distinguished by the bright Tyrian purple coloration of its inflorescence, which comprises a close cluster of about sixty florets carried on a strong, upright stem of about 10 to 12 cm. in length and extending well above a compact mass of foliage, the small to medium sized leaves of which have distinctive color zonation, the foliage mass extending about 14 cm. above the soil.

1 Drawing Sheet

BACKGROUND OF THE NEW PLANT

This new variety of geranium plant originated as a sport of the variety 'Cherry' (unpatented) grown at my nursery at Stuttgart, West Germany, and was discovered in 1986 among a group of geranium plants being grown for breeding purposes. This sport was selected for reproduction because of its apparently vigorous growth habit and purple coloration and asexual propagation of the sport was done by means of cuttings grown in greenhouse at Stuttgart. The plants resulting from this propagation of the new geranium appearing to have reasonable commercial merit, propagation has been continued for two years, both indoors and outdoors, by means of cuttings at Stuttgart, which demonstrated clearly that the novel characteristics would hold true from generation to generation and appear to be firmly fixed.

DESCRIPTION OF THE DRAWING

My new geranium cultivar is illustrated by the accompanying drawing, which shows the general character of the growing plant, as well as the color characteristic of the inflorescence, the drawing being a photographic print with color reproduction as nearly true as is reasonably possible to obtain by conventional photographic procedures.

DESCRIPTION OF THE NEW PLANT

The following is a detailed description of this new variety of geranium plant as observed at Stuttgart in 1988, with color designations according to The R.H.S. Colour Chart published by The Royal Horticultural Society at London, England.

THE PLANT

Origin: Sport.
Parent: Geranium variety 'Cherry' (unpatented).
Classification:
- *Botanic.*—*Pelargonium zonale hybrid.*
- *Commercial.*—Geranium.

Form: Bush.
Height: About 30 cm.
Main stem length: About 10 to 12 cm.
Growth: Vigorous and erect with normal branching and a medium growth rate.
Branching character: Normal.

Foliage:
- *Quantity.*—Abundant.
- *Size of leaf.*—Small to medium.
- *Leaf shape.*—Reniform with bicrenate margins.
- *Texture.*—Smooth.
- *Color.*—Upper side — Green with attractive zonation. Under side — A lighter green.

THE BUD

Size: Medium.
- *Diameter.*—About 11 mm.
- *Length.*—About 14 mm.

Shape: Generally ovoid with pointed apex.
Opening rate: Medium.
Color of petals:
- *When sepals first divide.*—Light pink.
- *When petals begin to unfurl.*—Violet purple.

Sepals:
- *Number.*—Five.
- *Character.*—The sepals stand up when flowers open.
- *Color.*—Inside — Green. Outside — Green.

Calyx:
- *Shape.*—Cup-shaped.
- *Size.*—Broad.
- *Splitting.*—The calyx does not split.
- *Aspect.*—Very slightly hairy.

Bud stem.
- *Character.*—Rigid.
- *Color.*—Green.

THE FLOWER

Blooming rate: Continuous and profusely from early spring to midseason.
Florets:
- *Number.*—About sixty in each umbel cluster.
- *Size.*—Medium. Diameter — About 4.5 cm. Depth — About 1 cm.
- *Borne.*—Singly on a stem of the umbel cluster.
- *Shape.*—When bloom first opens, cup-shaped. When bloom matures, flat cup.
- *Character.*—The Cap-shaped floret has an intensive red eye.

Petalage:
- *Number of petals.*—6 or 7.
- *Petal arrangement.*—Imbricated.

*Form.*—Broad with entire margins and a round apex.
*Texture.*—Soft.
*Appearance.*—Satiny.
*Color.*—Tyrian Purple, RHS 57-A.

Petaloids:
*Number.*—2 or 3.
*Size.*—About 5 to 8 mm.
*Color.*—Purple.

Flower stem:
*Length.*—About 10 to 12 cm.
*Color.*—Green.
*Character.*—Upright with good strength.

Persistence: The petals of the mature flowers hang on and dry.

Lasting quality: About 12 to 13 days.

REPRODUCTIVE ORGANS

Stamens:
*Number.*—Seven.
*Arrangement.*—In a ring around the pistil.
*Anthers.*—Size: About 1.5 mm. Color: Orange.
*Filaments.*—Length: About 4 mm. Color: Pink.

*Pollen.*—Color: Orange.

Pistil:
*Number.*—One.
*Style.*—Length: About 5 mm. Color: Frosted pink green.
*Stigma.*—Five lobed.
*Color.*—Frosted pink.

THE FRUIT

Fertility: The fruit is fertile.
Shape: Ovoid.
Color at maturity: Brown.

Due to its nice leaf zonation and its earliness, this plant is more attractive than 'Cherry' and its dark foliage assures a higher resistance to heat and humidity than seen in 'Cherry'.

I claim:

1. The new and distinctive cultivar of geranium, substantially as herein shown and described, particularly characterized by the Tyrian purple coloration of the flower mass of each cluster and the large size of the individual florets, each of which has a bright, shiny eye.

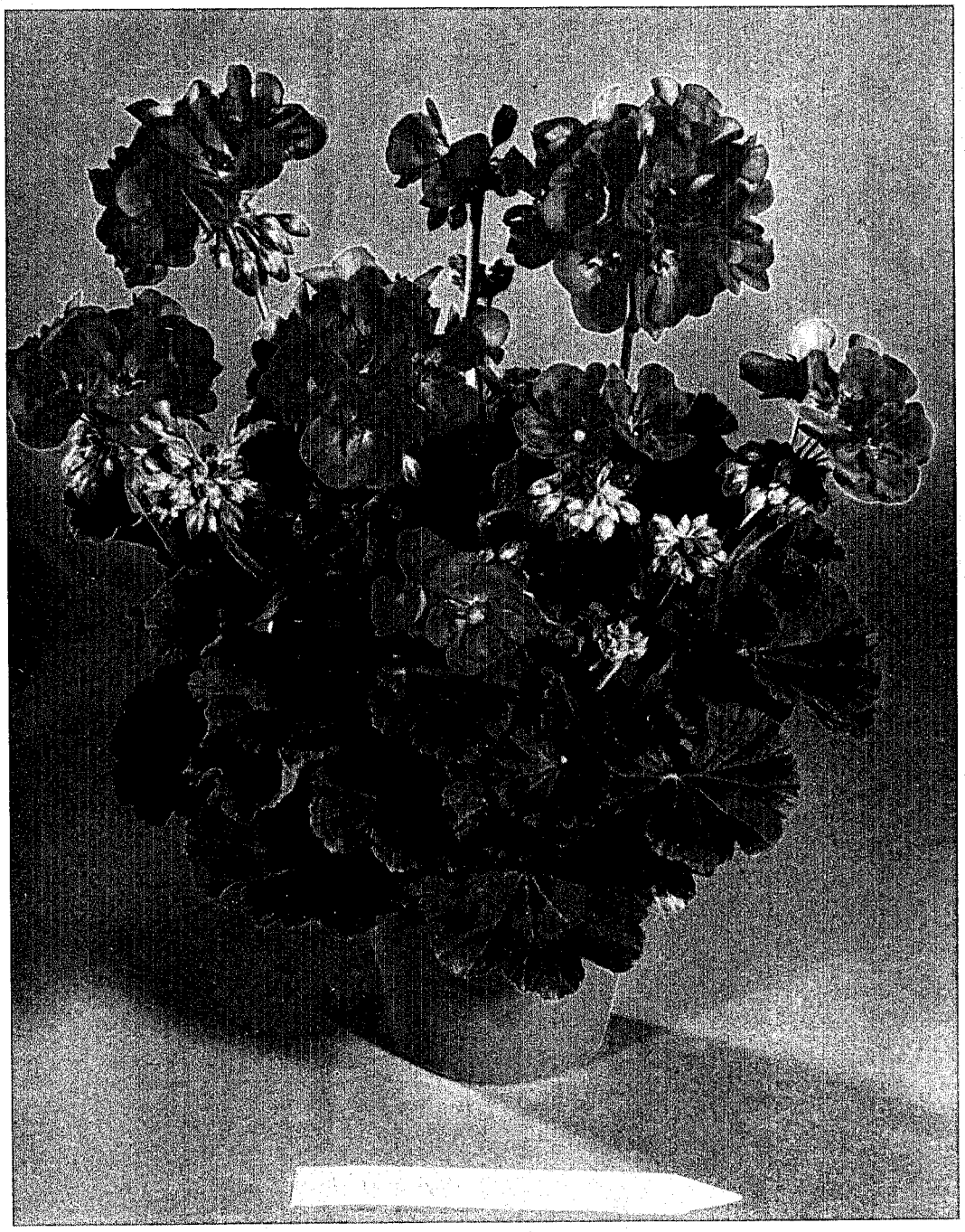

* * * * *